United States Patent
Riedel et al.

(10) Patent No.: US 8,852,176 B2
(45) Date of Patent: Oct. 7, 2014

(54) APPARATUS FOR OPTHALMOLOGICAL, IN PARTICULAR REFRACTIVE, LASER SURGERY

(75) Inventors: Peter Riedel, Nürnberg (DE); Christof Donitzky, Eckental (DE)

(73) Assignee: WaveLight GmbH, Erlangen (DE)

( * ) Notice: Subject to any disclaimer, the term of this patent is extended or adjusted under 35 U.S.C. 154(b) by 717 days.

(21) Appl. No.: 12/521,692

(22) PCT Filed: Jun. 30, 2008

(86) PCT No.: PCT/EP2008/005333
§ 371 (c)(1),
(2), (4) Date: Nov. 2, 2010

(87) PCT Pub. No.: WO2010/000279
PCT Pub. Date: Jan. 7, 2010

(65) Prior Publication Data
US 2011/0040292 A1    Feb. 17, 2011

(51) Int. Cl.
*A61B 18/20*    (2006.01)
*A61F 9/008*    (2006.01)

(52) U.S. Cl.
CPC .............. *A61F 9/008* (2013.01); *A61F 9/00825* (2013.01); *A61F 2009/00872* (2013.01); *A61F 9/00802* (2013.01); *A61F 2009/00846* (2013.01); *A61F 2009/0087* (2013.01); *A61F 2009/00851* (2013.01)
USPC .......... 606/5; 606/4; 606/10; 606/12; 351/208

(58) Field of Classification Search
USPC ................. 606/4–6, 10–12; 351/205–212
See application file for complete search history.

(56) References Cited

U.S. PATENT DOCUMENTS

| | | | |
|---|---|---|---|
| 6,712,809 B2 * | 3/2004 | Li et al. | 606/4 |
| 6,900,943 B2 * | 5/2005 | Andersen et al. | 359/618 |

(Continued)

FOREIGN PATENT DOCUMENTS

| | | |
|---|---|---|
| CN | 101094619 A | 12/2007 |
| JP | 2001-522279 | 11/2001 |

(Continued)

OTHER PUBLICATIONS

Office Action and translation received from Chinese Patent Office for Chinese Patent Application No. 200880130165.3, dated Sep. 5, 2012, 13 pages.

(Continued)

*Primary Examiner* — Ahmed Farah
(74) *Attorney, Agent, or Firm* — Haynes and Boone, LLP

(57) ABSTRACT

An apparatus for ophthalmological, in particular refractive, laser surgery includes a laser-beam source (20) for emitting a focused treatment laser beam (20') and also includes an optical-coherence interferometric measuring device (34), for example an OLCR pachymeter, for measuring the z-position of a predetermined point of an eye to be treated in the coordinate system of the laser-surgery apparatus. A computer (C) serving as evaluating and control unit has been set up to assess, on the basis of the measured z-position, whether a desired treatment point of the eye in the z-direction falls in the focal plane of the treatment laser beam or is offset in relation to said plane. Depending on whether or not the patient is correctly positioned in relation to the focal plane, the computer (C) can bring about a range of actions.

19 Claims, 1 Drawing Sheet

(56) References Cited

U.S. PATENT DOCUMENTS

| | | |
|---|---|---|
| 2005/0018137 A1 | 1/2005 | Barth |
| 2005/0024586 A1* | 2/2005 | Teiwes et al. .............. 351/209 |
| 2005/0140981 A1 | 6/2005 | Waelti |
| 2006/0100613 A1 | 5/2006 | McArdle et al. |
| 2006/0106371 A1* | 5/2006 | Muhlhoff et al. .............. 606/5 |
| 2006/0195076 A1 | 8/2006 | Blumenkranz et al. |

FOREIGN PATENT DOCUMENTS

| | | |
|---|---|---|
| JP | 2002-518093 | 6/2002 |
| JP | 2005-536312 | 2/2005 |
| JP | 2009-529357 | 8/2009 |
| WO | WO 98/48746 | 11/1998 |
| WO | WO 99/65431 | 6/1999 |
| WO | 9965431 | 12/1999 |
| WO | 0119303 A1 | 3/2001 |
| WO | WO 2004/026198 | 4/2004 |
| WO | WO-2006/090217 | 8/2006 |
| WO | WO-2007/016231 | 2/2007 |
| WO | WO 2007/104448 | 9/2007 |
| WO | 2008087483 A1 | 7/2008 |

OTHER PUBLICATIONS

European Patent Office, Office Action dated Aug. 14, 2008, Application No. PCT/US2008/055842, 7 pages.

Japanese Patent Office, Office Action and translation received for Japanese Patent Application No. 2011-515115, dated Dec. 14, 2012, 6 pages.

Korean Patent Office, Office Action and translation received for Korean Patent Application No. 10-2011-7002554, dated Jan. 14, 2013, 9 pages.

* cited by examiner

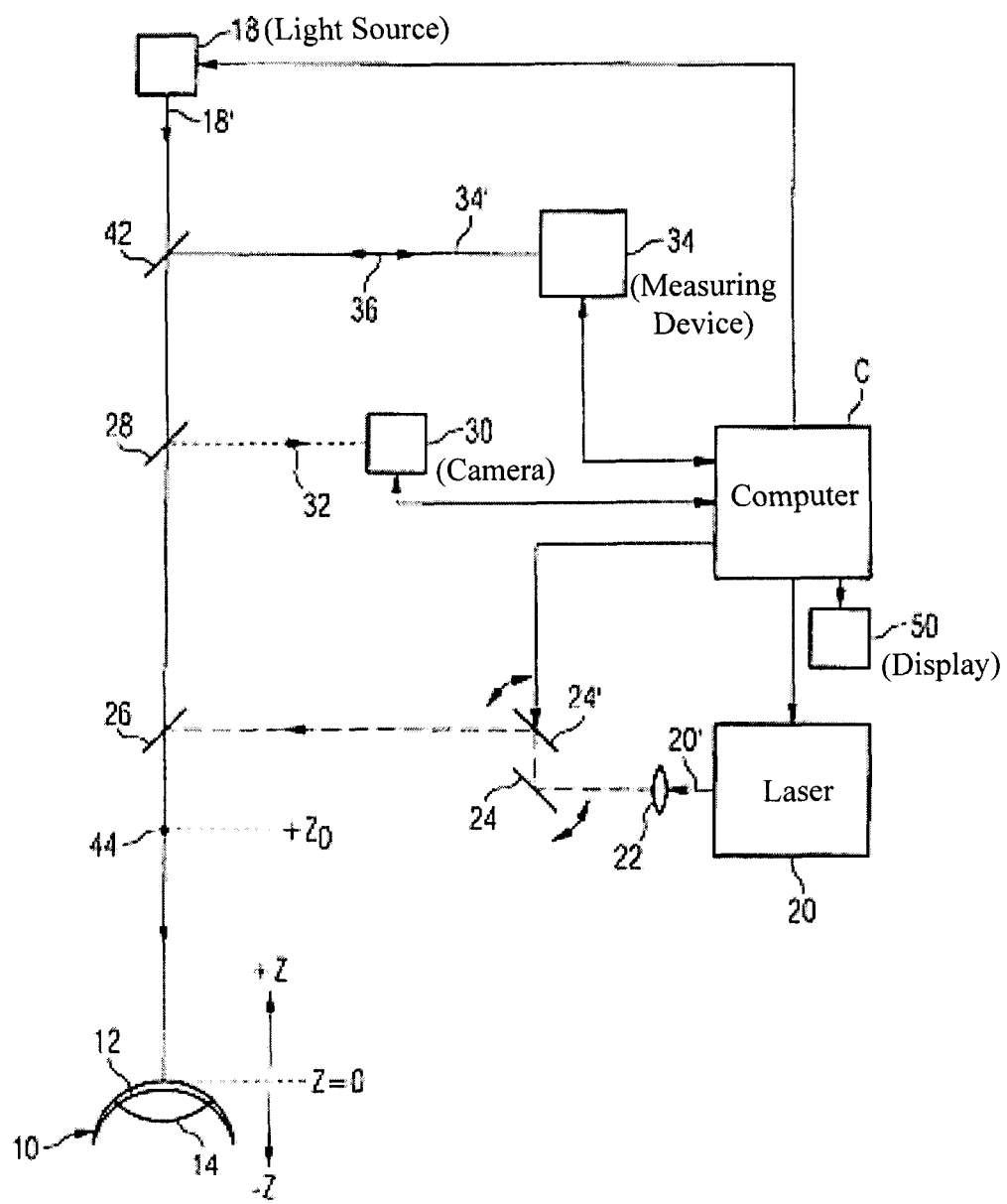

APPARATUS FOR OPTHALMOLOGICAL, IN PARTICULAR REFRACTIVE, LASER SURGERY

CROSS REFERENCE

This application was originally filed as Patent Cooperation Treaty Application Number PCT/EP2008/005333 on Jun. 30, 2008.

CROSS-REFERENCE TO RELATED APPLICATION

This application is a United States national phase application of co-pending international patent application number PCT/EP2008/005333, filed Jun. 30, 2008, the disclosure of which is incorporated herein by reference.

SUMMARY

The invention relates to an apparatus for ophthalmological, in particular refractive, laser surgery.

In surgery involving the human eye there are numerous treatment methods in which laser radiation is directed onto the eye in order to obtain an indicated aim of treatment as a consequence of the interaction of the radiated laser radiation with the eye. In the case of refractive laser surgery, the aim of treatment is an alteration, by means of the laser radiation, of the imaging properties of the optical system constituted by the eye. Since the cornea, above all, is crucial for the imaging properties of the human eye, in many cases refractive laser surgery of the eye includes a treatment of the cornea. By targeted introduction of incisions and/or by targeted resection of material, in these processes a change of shape of the cornea is brought about; one therefore also speaks of a reshaping.

A known example of a reshaping of the cornea for the purpose of altering its refractive properties is LASIK (laser in-situ keratomileusis). In the case of LASIK, a superficial cover disc, which in specialist circles is generally designated as a flap, is cut out of the cornea. On a part of its edge in a hinge region the flap is still connected to the corneal tissue situated alongside, so that it can be folded aside and later folded back again without difficulty. For the purpose of producing the flap, in prior practice two methods in particular have found application, on the one hand a mechanical method by means of a microkeratome, and on the other hand a laser-technology method, wherein by means of femtosecond laser radiation (i.e. pulsed laser radiation with a pulse duration within the fs range) a planar depth incision is introduced into the cornea, which, except for the hinge region, is guided out to the corneal surface. After the flap that has been produced has been folded away, a resection of material (ablation) from the stroma which has been exposed in this way is effected in accordance with an ablation profile previously established for the patient. The ablation profile specifies at which point of the cornea how much tissue is to be resected. It is calculated in such a way that, after the ablation, the cornea has a shape that is optimal for the eye being treated and the previously existing optical aberrations of the eye are corrected as extensively as possible. An excimer laser, for example, with a radiation wavelength in the UV region, at approximately 193 nm, finds application for the ablation.

For the implementation of the ablation—or, generally speaking, for the implementation of a laser treatment of the eye—the patient firstly has to be suitably positioned, so that his/her eye has a certain working distance from the laser apparatus. A photodisruptive or ablating interaction of the laser radiation with the tissue being treated arises solely in the region of the beam focus. The working distance should therefore be chosen in such a way that the point of the eye that is to be treated is situated substantially in the plane of the beam focus (by the expression 'plane of the beam focus' here the plane is meant that is situated perpendicular to the beam direction and that passes through the beam focus). If the head of the patient is not correctly positioned relative to the plane of the beam focus, the beam diameter increases at the point of the eye where the desired treatment is to take place. The irradiance decreases correspondingly—i.e. less energy per surface area is radiated. This may result in an inadequate ablation and in irregularities in the resection. Ultimately an aggravated result of treatment arises.

For the purpose of orienting the patient in relation to the laser apparatus, a manner of proceeding has become known in which two intersecting auxiliary beams of light are directed onto the eye to be treated from above, laterally. The sources of these auxiliary beams of light—for example, weak laser diodes—are arranged in such a way that the corneal reflections of the auxiliary beams of light combine at a common point on the surface of the cornea, provided that the eye is precisely positioned at the desired working distance from the laser apparatus. In the case of a faulty positioning of the patient, on the other hand, two individual reflections are visible on the cornea, one from each auxiliary beam of light. This holds both when the patient is located too close to the laser apparatus and when he/she is located too far away. In one case, the point of intersection of the auxiliary beams of light is situated in front of the cornea; in the other case, behind it. This shows that although the correct positioning of the patient can be recognised with the two auxiliary beams of light, in the case of a faulty positioning it cannot be readily discerned in which direction the deviation is going. This can only be found out by the patient being displaced in the manner of a test. If in one direction of displacement no approximation of the reflections takes place, he/she has to be displaced in the other direction. Moreover, it cannot be readily discerned how great the deviation of the patient is from the optimal working position. Although the mutual spacing of the reflections on the cornea can be a rough guide under certain circumstances, it does not permit quantitative statements of any kind.

The above difficulties for the treating physician in assessing the direction and extent of a faulty positioning of the patient precisely from the image of the reflections on the cornea ultimately lead to numerous adjusting movements which have to be performed in respect of the patient's couch in order to discover the optimal working distance for the patient.

The object of the invention is to simplify the precise positioning of the patient for the ophthalmological laser surgery.

With a view to achieving this object, in accordance with the invention an apparatus for ophthalmological, in particular refractive, laser surgery is provided, with a laser-beam source for emitting a focused treatment laser beam, an optical-coherence interferometric measuring device for measuring the distance of a predetermined point or region of an eye to be treated from a reference point which is in a known relationship to the focal position of the treatment laser beam, and an evaluating and control unit which has been set up to register, on the basis of the measured distance data of the measuring device, the coincidence or divergence of a desired location of action of the treatment laser beam on or in the eye and of the focal position of the treatment laser beam, and in the case of coincidence or/and divergence to bring about a predetermined output action.

Optical-coherence interferometric measuring devices have been available for some time for non-contacting surveying of eye parameters, for example the thickness of the cornea or the depth of the anterior chamber. Such measuring devices operate, for example, in accordance with the principle of optical low-coherence reflectometry (OLCR) or in accordance with the principle of optical coherence tomography (OCT). They work with low-coherence, broadband measuring radiation and permit structures of the eye (or generally of the biological tissue to be surveyed) to be surveyed with a resolution in the region of 1 μm and finer. In this connection, OLCR is also suitable, in particular, for measurements of the distance between the eye and the laser-surgery apparatus. Therefore in the invention the measuring device is preferentially based on OLCR.

The invention teaches the integration of a measuring device of the above type into a laser-surgery apparatus and the utilisation of the measuring device for the purpose of orienting the patient. The measured data of an OLCR measuring device or other interferometric measuring device permit the determination of the direction and extent of a deviation of the actual distance of the patient from the optimal working distance, and consequently make the adjustment of the patient simpler. The measuring device expediently measures the distance of the eye from the reference point in the direction of the treatment laser beam (z-direction). The reference point is a given point that is unambiguously capable of being localised in the coordinate system of the laser-surgery apparatus—for example, the origin of coordinates or a point that is different from the origin. The beam focus of the treatment laser beam is likewise set with respect to the coordinate system of the laser-surgery apparatus. In this way, from the measured eye distance and the z-position of the beam focus the evaluating and control unit can ascertain the z-distance of the eye from the focal plane. In particular, the evaluating and control unit can ascertain whether the desired location of action of the treatment laser beam falls in the focal plane or is offset in relation to the latter.

The point or region of the eye from which the measuring device measures the distance from the reference point lies, for example, on the corneal surface of the eye. If the laser treatment is to take place close to the surface—as is the case, for instance, in the course of the ablation within the scope of LASIK—then the desired location of action, to which the focal plane or treatment plane of the treatment laser beam has to be adjusted, may be regarded as substantially the same as the measuring point of the eye, the distance of which from the reference point is being measured. It may also be the case that a point situated below the corneal surface is drawn upon by way of target point for the distance measurement, for example in the case of femtosecond LASIK.

However, the invention is by no means restricted to a laser-surgery apparatus for LASIK. It is just as applicable in the case of laser-surgery apparatuses for other ophthalmological treatment purposes. Accordingly, it may be the case that the desired location of action of the treatment laser beam is a location in the eye other than the point from which the distance from the reference point is measured. As stated, a point on the corneal surface, for instance the apex of the cornea, is suitable, for example, for the distance measurement. The desired location of action of the treatment laser beam may, on the other hand, be situated deeper within the eye, for instance on the lens. In this case it is expedient to take account of the z-distance between the measuring point of the eye and the desired location of action when orienting the patient. On the assumption that this z-distance is known, for instance by virtue of a preceding OLCR survey of the eye, from the measured distance of the eye from the reference point, from the known relative position of the beam focus in relation to the reference point and from the likewise known z-distance between the measuring point of the eye and the desired location of action the evaluating and control unit can readily establish whether or not the focal plane coincides with the desired location of action in the z-direction.

Various output actions of the evaluating and control unit are conceivable if a coincidence, or a divergence, of the desired location of action with/from the focus in the z-direction is established. For documentation and logging of the relative position of the focal plane (treatment plane) relative to the desired location of action of the treatment laser beam, one form of output action of the evaluating and control unit may consist in the output of storage commands or display commands which bring about a storage or display of the results of measurement on a display unit. Such documentation is particularly expedient when several distance measurements are carried out during the laser treatment, for example at regular temporal intervals. For it cannot be ruled out that during the laser surgery the patient moves his/her head and in this way brings about a faulty orientation which should not remain concealed from the operator. The stored results of measurement may, where required, be printed out or used otherwise subsequent to the operation. An immediate display of the currently measured distance in the given case on a display unit furnishes the operator with a checking option which permits him/her, where required, to intervene in the treatment procedure in correcting manner or even to interrupt said procedure under certain circumstances.

In one embodiment of the invention an automation is provided to the effect that the evaluating and control unit can, in response to the result of the distance measurement, output a control command to the laser-beam source in order to control the emission of the treatment laser beam. For example, such a control command may permit the emission of the treatment laser beam only on the condition that the desired location of action and the focal position substantially coincide. This is expedient in order to guarantee that the laser surgery is commenced only when the patient is correctly oriented. Alternatively or in addition, the evaluating and control unit may have been set up to emit control commands that bring about an interruption of the emission of the treatment laser beam if the distance measurement shows that the desired location of action and the focal position diverge. In this way the evaluating and control unit can automatically interrupt the laser surgery if the patient moves his/her head during the treatment.

Of course, various other types of output action of the evaluating and control unit are conceivable. For example, the evaluating and control unit may have been set up to bring about the output of an optical or/and acoustic signal message if a coincidence or a divergence of the desired location of action and of the focal position is established within the scope of the distance measurement.

BRIEF DESCRIPTION OF THE DRAWING

The invention will be elucidated further in the following on the basis of the appended single drawing. The latter shows schematically an exemplary embodiment of a laser-surgery apparatus according to the invention, which is suitable, in particular but not exclusively, for the implementation of the ablation in the course of LASIK.

DETAILED DESCRIPTION

Represented first of all in the drawing is a human eye 10 with a cornea 12 and with a pupillary margin 14.

The laser-surgery apparatus that is shown exhibits, in a manner known as such, a source of fixation light (e.g. LED, laser) 18 which emits a (weak) beam of fixation light 18' and is sighted by the patient for the purpose of fixing the eye.

Furthermore, the laser-surgery apparatus includes a treatment laser 20 which emits a treatment laser beam 20' which is directed via a lens 22 towards a pair of scanner mirrors 24, 24' and is deflected onto the eye 10 via a partially transmitting deflecting mirror 26. The treatment laser beam 20' is a focused laser beam; focusing optics for focusing the treatment laser beam 20' are not represented in any detail in the drawing. Suitable focusing optics are, however, sufficiently known as such in the state of the art.

The laser 20 is for example, an excimer laser, the radiation wavelength of which lies within the UV region, for instance at 193 nm. It will be understood that, for other treatment purposes, other treatment wavelengths may be used where desired, also in the infrared region. For example, for the laser 20 use may also be made of a femtosecond laser which radiates in the UV or IR wavelength region.

The scanner mirrors 24, 24' are, for example, galvanometrically actuated and are controlled together with the laser 20 by a program-controlled computer C in accordance with a previously calculated treatment profile (i.e. an ablation profile or—in the case of an incisional laser treatment—an incision profile). The computer C constitutes an evaluating and control unit in the sense of the invention.

The laser-surgery apparatus possesses furthermore a device for tracking eye movements (eye-tracker). The eye-tracker includes a camera 30, with which images of the eye— in concrete terms, of the pupil and of the iris—can be recorded via a partially transmitting deflecting mirror 28 in the direction of an arrow 32. The image data of the camera 30 are then evaluated in the computer C by means of image-analysis software, in order to track movements of the eye which the patient, as a rule, cannot avoid, despite the attempted fixation of the eye onto the fixation light 18'. The detected eye movements are taken into account by the computer C in the control of the scanner mirrors 24, 24', in order in this way to keep the treatment profile oriented as constantly as possible in relation to a predetermined reference point of the eye, which is situated, for example, on the corneal surface.

Integrated into the laser-surgery apparatus is, in addition, a pachymeter measuring device 34 for optical low-coherence reflectometry (OLCR), which includes, in a manner known as such, a radiation source (e.g. SLED, ASE, supercontinuum laser) which emits a measuring beam 34'. The measuring beam is directed onto the eye 10 via a partially transmitting deflecting mirror 42, namely in such a way that it impinges on the eye coaxially relative to the beam path of the treatment laser beam 20'. The measuring device 34 receives measuring radiation reflected from the eye 10 via the deflecting mirror 42 on the same path on which the measuring beam 34' is emitted by the measuring device 34. This is illustrated by a double-headed arrow 36.

Within the scope of a treatment to be carried out by means of the laser-surgery apparatus subject to control of the computer C, the measuring device 34 measures at least once, preferentially several times, the distance of the eye 10 in the direction of the beam axis of the part of the treatment laser beam 20' (z-direction) impinging on the eye from a predetermined reference point in the coordinate system of the laser-surgery apparatus. For the purpose of illustration, the reference point in the drawing is indicated at 44. Said point is located at a z-position $+z_0$, the value of which is known. A point on the corneal surface, for example the apex, preferentially serves as measuring point on the eye 10.

The measuring device 34 supplies its measured distance data to the computer C, which compares the measured z-distance between the measuring point of the eye and the reference point 44, which is fixed with respect to the coordinate system, with the z-distance between the beam focus of the laser treatment beam 20' and the reference point 44. The z-position of the beam focus is predetermined by the setting of the aforementioned focusing optics and is known to the computer C. In the present case let it be assumed in exemplary manner that the beam focus is set to a position at $z=0$. If the distance comparison shows that the part of the eye 10 to be treated lies in the focal plane of the treatment laser beam 20', the computer C enables, for example, the laser 20, so that the laser surgery can begin. If, however, the distance comparison shows that the eye 10 is not correctly positioned in the z-direction—i.e. the part of the eye to be treated does not lie in the focal plane—then the computer C brings about, for example, a display of the need for adjustment on a display device 50. The displayed need for adjustment specifies to the operator the direction and extent of the necessary z-adjustment of the patient. The operator can then head for the optimal patient position by vertical adjustment of a patient couch on which the patient is lying. In this connection it is expedient if the measuring device 34 carries out further distance measurements continuously and the computer C displays on the display unit 50 the current z-position of the eye 10 in the given case relative to the focal plane, in order to enable for the operator an immediate monitoring of the success of his/her adjustment efforts. As soon as the patient has been positioned in such a way that the desired treatment point of the eye and the beam focus in the z-direction substantially coincide, this can be additionally communicated to the operator, for example by means of a readily audible signal tone.

It is, of course, also possible to couple the adjusting mechanism of the patient's couch with the computer C in such a manner that the computer C can carry out an automatic z-adjustment of the couch in program-controlled manner, depending on the current result of measurement in the given case.

It was mentioned above that the distance between a given eye point and a fixed reference point in the coordinate system of the laser-surgery apparatus is measured within the scope of the distance measurement. This is tantamount to a measurement of the z-position of the given eye point in the coordinate system of the laser system, since each specification of a z-position always needs a point of reference, namely the origin of the coordinate system. To this extent it is possible to state in simplified terms that the measuring device 34 measures the z-position of the given eye point, for example the corneal apex, and the computer C compares the measured z-position of this eye point with the z-position of the beam focus. The indication of the reference point in the course of the distance measurement is, to this extent, nothing more than a clarification that each statement of an absolute coordinate position is also to be interpreted always as a distance from a reference point of the coordinate system.

The invention claimed is:

1. Apparatus for ophthalmological laser surgery, comprising:
    a laser-beam source for emitting a focused treatment laser beam,
    an optical-coherence interferometric measuring device for measuring the distance of a predetermined point or region of an eye to be treated from a reference point which is in a known relationship to the focal position of the treatment laser beam, and
    an evaluating and control unit which has been set up to register, on the basis of the measured distance data of the measuring device, the coincidence or divergence of a desired location of action of the treatment laser beam on or in the eye and of the focal position of the treatment laser beam and in the case of coincidence or divergence to bring about a predetermined output action, wherein the predetermined output action in the case of coincidence or divergence includes a display of a needed adjustment of a patient positioning in order for the desired location of action of the treatment laser beam on or in the eye to coincide with the focal position of the treatment laser, wherein the display of the needed adjustment includes both a direction and a distance necessary for the desired location of action of the treatment laser beam on or in the eye to coincide with the focal position of the treatment laser.

2. Apparatus according to claim 1, wherein the measuring device has been set up to measure the distance of a point on or below the corneal surface of the eye to be treated from the reference point.

3. Apparatus according to claim 1, wherein the evaluating and control unit has been set up to store the results of distance measurements carried out during the laser treatment of the eye.

4. Apparatus according to claim 1, wherein the evaluating and control unit has been set up to permit the emission of the treatment laser beam depending on the fact that the desired location of action and the focal position substantially coincide.

5. Apparatus according to claim 4, wherein the evaluating and control unit has been set up to interrupt the emission of the treatment laser beam depending on the fact that the desired location of action and the focal position diverge.

6. Apparatus according to claim 1, wherein the measuring device measures the distance by optical low-coherence reflectometry.

7. Apparatus according to claim 1, wherein the laser-beam source is an excimer laser radiating in the UV wavelength region or a femtosecond laser radiating in the UV or IR wavelength region.

8. Apparatus according to claim 1, further comprising an adjusting mechanism configured to impart vertical adjustment of a structure on which the patient is lying.

9. Apparatus according to claim 8, wherein the adjusting mechanism is in communication with the evaluating and control unit and wherein the evaluating and control unit is configured to automatically control the adjusting mechanism based on the needed adjustment.

10. Apparatus according to claim 1, wherein the evaluating and control unit is configured to continuously display the needed adjustment of the patient positioning in order for the desired location of action of the treatment laser beam on or in the eye to coincide with the focal position of the treatment laser during a procedure.

11. Apparatus according to claim 1, wherein the evaluating and control unit is further configured to provide an indication that the desired location of action of the treatment laser beam on or in the eye coincides with the focal position of the treatment laser during a procedure.

12. Apparatus according to claim 11, wherein the indication that the desired location of action of the treatment laser beam on or in the eye coincides with the focal position of the treatment laser during a procedure is an audible signal.

13. A method of performing ophthalmological laser surgery, comprising:
providing a laser-beam source for emitting a focused treatment laser beam and an optical-coherence interferometric measuring device;
defining a reference point and a predetermined point on an eye to be treated;
determining the distance between the reference point and the predetermined point utilizing the measuring device;
evaluating the distance data to register coincidence or divergence of the treatment laser beam at the predetermined location;
displaying, based on the determined distance between the reference point and the predetermined point, a needed adjustment of a patient positioning in order for a desired distance between the reference point and the predetermined point to be achieved, wherein displaying the needed adjustment includes both a direction and a distance necessary for the desired distance between the reference point and the predetermined point to be achieved; and
controlling the treatment laser beam based on said evaluating to bring about a predetermined output action at the predetermined location.

14. The method of claim 13, further comprising adjusting the patient positioning.

15. The method of claim 14, wherein adjusting the patient positioning includes vertical adjustment of a structure on which the patient is lying.

16. The method of claim 15, wherein the vertical adjustment is automatically controlled by a control program based on the needed adjustment.

17. The method of claim 14, further comprising repeating the determining, evaluating, and displaying steps while adjusting the patient positioning.

18. The method of claim 13, wherein controlling the treatment laser beam includes permitting the emission of the treatment laser beam when the desired distance between the reference point and the predetermined point is achieved.

19. The method of claim 18, wherein controlling the treatment laser beam includes interrupting emission of the treatment laser beam when the desired distance between the reference point and the predetermined point is not achieved.

* * * * *

UNITED STATES PATENT AND TRADEMARK OFFICE
CERTIFICATE OF CORRECTION

PATENT NO. : 8,852,176 B2  
APPLICATION NO. : 12/521692  
DATED : October 7, 2014  
INVENTOR(S) : Peter Riedel et al.

Page 1 of 1

It is certified that error appears in the above-identified patent and that said Letters Patent is hereby corrected as shown below:

On the Title Page

In the title:

"Opthalmological" should read -- Ophthalmological --

Signed and Sealed this
Seventeenth Day of February, 2015

Michelle K. Lee
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,852,176 B2 | Page 1 of 1 |
| APPLICATION NO. | : 12/521692 | |
| DATED | : October 7, 2014 | |
| INVENTOR(S) | : Peter Riedel et al. | |

It is certified that error appears in the above-identified patent and that said Letters Patent is hereby corrected as shown below:

On the Title Page and in the Specification, Column 1, line 1,

In the title:

"Opthalmological" should read -- Ophthalmological --

This certificate supersedes the Certificate of Correction issued February 17, 2015.

Signed and Sealed this
Tenth Day of March, 2015

Michelle K. Lee
*Deputy Director of the United States Patent and Trademark Office*